(12) United States Patent
Coats et al.

(10) Patent No.: US 10,231,702 B2
(45) Date of Patent: *Mar. 19, 2019

(54) ECHOGENIC ARTICLE WITH COMPOUND INDENTATIONS

(71) Applicant: Avent, Inc., Alpharetta, GA (US)

(72) Inventors: Alfred C. Coats, Houston, TX (US); Louis Lupin, Houston, TX (US)

(73) Assignee: Avent, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/106,878

(22) Filed: Aug. 21, 2018

(65) Prior Publication Data

US 2018/0353155 A1     Dec. 13, 2018

Related U.S. Application Data

(63) Continuation of application No. 14/308,038, filed on Jun. 18, 2014, now Pat. No. 10,076,307.

(60) Provisional application No. 61/837,455, filed on Jun. 20, 2013.

(51) Int. Cl.
| | |
|---|---|
| *A61B 8/00* | (2006.01) |
| *A61M 25/01* | (2006.01) |
| *A61B 17/34* | (2006.01) |
| *A61B 90/00* | (2016.01) |
| *A61B 34/20* | (2016.01) |

(52) U.S. Cl.
CPC .............. *A61B 8/445* (2013.01); *A61B 90/39* (2016.02); *A61M 25/0108* (2013.01); *A61B 34/20* (2016.02); *A61B 2017/3413* (2013.01); *A61B 2034/2063* (2016.02); *A61B 2090/3925* (2016.02); *A61M 2205/3375* (2013.01)

(58) Field of Classification Search
None
See application file for complete search history.

(56) References Cited

U.S. PATENT DOCUMENTS

| | | | |
|---|---|---|---|
| 5,081,997 A * | 1/1992 | Bosley, Jr. ............. | A01K 85/00 424/9.4 |
| 5,759,154 A | 6/1998 | Hoyns | |
| 7,057,832 B2 | 6/2006 | Wu et al. | |
| 2003/0153804 A1 | 8/2003 | Tornes et al. | |
| 2004/0249288 A1 | 12/2004 | Ichikawa et al. | |
| 2008/0097213 A1* | 4/2008 | Carlson .................. | A61B 5/064 600/458 |

(Continued)

FOREIGN PATENT DOCUMENTS

WO     WO 2008/148165 A1     12/2008

*Primary Examiner* — Katherine Fernandez
*Assistant Examiner* — Michael Kellogg
(74) *Attorney, Agent, or Firm* — Dority & Manning, P.A.

(57) ABSTRACT

The present invention provides an article or an interface having a distribution of a first partially spherical indentation and at least a second partially spherical indentation contained within the first indentation to form a multi-component or "compound" shape that is referred to as a "compound" or "nested" dimples or indentations. These compound dimples or indentions may be concentric and are etched or otherwise formed into a surface or interface of an article to enhance the ultrasonic imaging. Exemplary articles may be needles of the type used to conduct nerve blocks or the interface may be the surface of such a needle, cannula, catheter, catheter tip or similar article.

9 Claims, 4 Drawing Sheets

(56) References Cited

U.S. PATENT DOCUMENTS

| | | | |
|---|---|---|---|
| 2009/0030391 A1 | 1/2009 | Hammons et al. | |
| 2011/0046619 A1* | 2/2011 | Ducharme | A61B 18/1477 |
| | | | 606/41 |
| 2012/0059247 A1 | 3/2012 | Speeg et al. | |

* cited by examiner

ECHOGENIC ARTICLE WITH COMPOUND INDENTATIONS

RELATED APPLICATIONS

This application claims the benefit of priority from U.S. Provisional Application No. 61/837,455 filed on Jun. 20, 2013 and is a continuation of U.S. application Ser. No. 14/308,038 filed on Jun. 18, 2014, both of which are incorporated by reference herein in their entirety.

FIELD OF THE INVENTION

The present invention relates generally to echogenic devices and methods and particularly to echogenic devices, material and methods, which among other applications may be used with medical devices that are insertable into a medium such as biological tissue and imageable with sonic imaging equipment

BACKGROUND

Ultrasonic imaging in the medical field is widely used for a variety of applications. In addition to imaging physiological structures and tissue such as organs, tumors, vessels, and the like, it is often desirable for a physician or technician to have an image of a medical device which has been inserted into the tissue or passageway of a patient. The types of devices which are surgically sterilized and inserted into patients are many. Typical examples include: needles, catheters and a variety of other medical products such as stents, dilators, pacing leads, introducers, angiography devices, angioplasty devices, pacemakers, in-patient appliances such as pumps and other devices. Various approaches have been used to enhance ultrasonic imaging by modifying the reflective surface characteristics of these devices.

U.S. Pat. No. 5,081,997 to Bosley, Jr. et al, for "Echogenic Devices, Material and Method" discloses a device such as a needle that includes an interface having a shape that is formed with a dimension that is less than a wavelength of the incident sonic beam. According to Bosley, Jr. et al., the shape includes a dimension such as a radius of curvature which is much less than the wavelength of the sonic beam. The interface may include the outside surface a device or article or material. That surface has a plurality of partially spherical indentations for producing a scattered component of the image in response to the incident beam. This image is produced regardless of the incident beam angle of which conventional devices depend for producing a reflected or constructive interference image. The scattered component of the image is produced when the radius of the partially spherical indentations or a dimension of another geometric shape or surface are much less than the wavelength of the incoming sonic beam.

Conventional recesses or dimples frequently have faces, bottoms and sides that are generally flat. For example, FIGS. 1-4 are photomicrographs illustrating a portion of an echogenic region from an EchoTip® needle available from Cook Medical, Bloomington, Ind. As can be seen in these photomicrographs, the echogenic region contains recesses or dimples having generally flat bottoms and sides that are generally perpendicular to the needle surface and to the recess or dimple bottom. The recess or dimple bottom has a small groove which is believed to be an artifact of machining.

U.S. Patent Application Publication No. 2004/0249288 A1 to Ichikawa for "Ultrasonic Puncture Needle" discloses a device including an array of doughnut shaped recesses having a center portion remaining as a protrusion. According to US Publication No. 2004/0249288 A1, the recesses are also formed with faces, bottoms and sides being generally flat so to obtain reflection echoes with a great intensity for the incident ultrasonic waves with a shallow incident angle.

While the approaches described in U.S. Pat. No. 5,081, 997 and U.S. Publication No. 2004/0249288 A1 have shown promise, improvements have been sought that would result in an interface that provides enhanced ultrasonic imaging, in a manner that is inexpensive to manufacture, and simple and reliable to use.

SUMMARY OF THE INVENTION

In response to the difficulties and problems discussed herein, the present invention provides an article or an interface having a distribution of a first partially spherical indentation and at least a second partially spherical indentation contained within the first indentation. Such a multi-component or "compound" shape may be referred to as a "compound" or "nested" dimples or indentations. These "compound dimples" or indentations are etched or otherwise formed into a surface or interface of an article to enhance the ultrasonic imaging. Exemplary articles may be needles of the type used to conduct nerve blocks or the interface may be the surface of such a needle, cannula, catheter, catheter tip or similar article.

Generally speaking, the dimple or indention is composed of at least a first partially spherical indentation and a second partially spherical indentation contained within the first indentation. The present invention contemplates compound dimples that may include at least a first partially spherical indentation and a second and third (or more) partially spherical indentation contained within the first indentation. Alternatively and/or additionally, the present invention contemplates compound dimples that may include at least a first partially spherical indentation and a second partially spherical indentation contained within the first indentation and a third (or more) partially spherical indentation contained within the second indentation.

In an aspect of the invention, the first (or major) partially spherical indentation or "dimple" may have a diameter ranging from about approximately 0.003 to approximately 0.006 inch. The second (or minor) partially spherical indentation or "internal dimple" may have a diameter of up to about 0.0025 inch. For example, the second (or minor) partially spherical indentation or "internal dimple" may have a diameter of from about 0.0005 to about 0.0025 inch. Additional partially spherical indentations contained within the first partially spherical indentation and/or the second partially spherical indentation should be smaller. In an aspect of the invention, the spacing between the edges of the major partially spherical indentations or dimples may be about 0.004 inch apart. In another aspect of the invention, the depth of the spherical indentations may be from about 0.0005 to about 0.005 inch.

The "compound" structure of nested partially spherical indentations or dimples may be manufactured in a process using a laser. The second (or minor) partially spherical indentations or dimples are generated during the manufacturing process by spatter, displacement of metal and other phenomena. This "compound" or nested structure is thought to increase Rayleigh Scattering of the ultrasonic wave which significantly increases the echogenicity of an article (e.g., a needle) having a distribution of these "compound dimples".

When the indentation is substantially smaller than the wavelength of the ultrasonic beam, Rayleigh Scattering occurs.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the invention with reference to the accompanying drawing figures, in which like reference numerals denote similar structure and refer to like elements throughout, and in which.

The article is the shaft of a cannula or needle.

Figure 1:
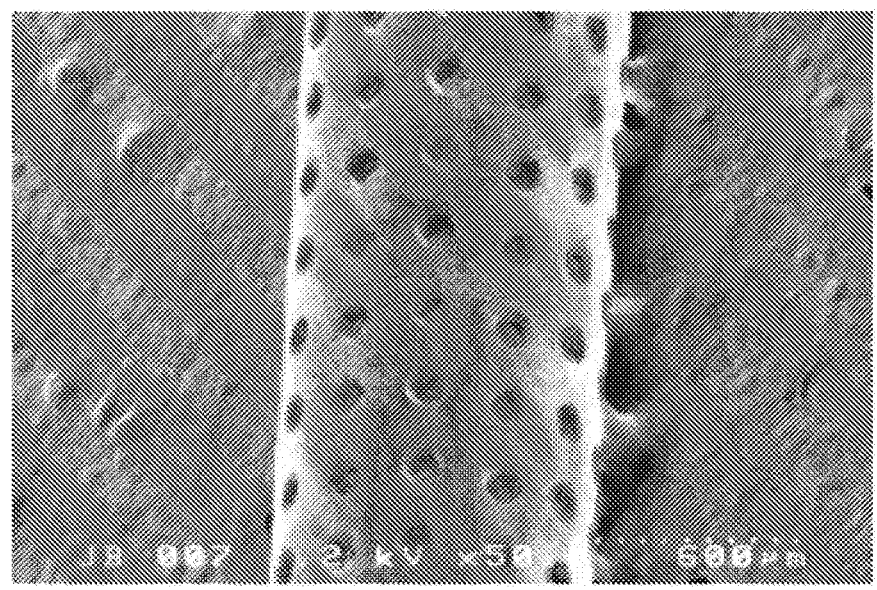
FIG. 1 is a scanning electron photomicrograph at 50× linear magnification of a surface illustrating an article having a distribution of conventional dimples or recesses.
Figure 2:
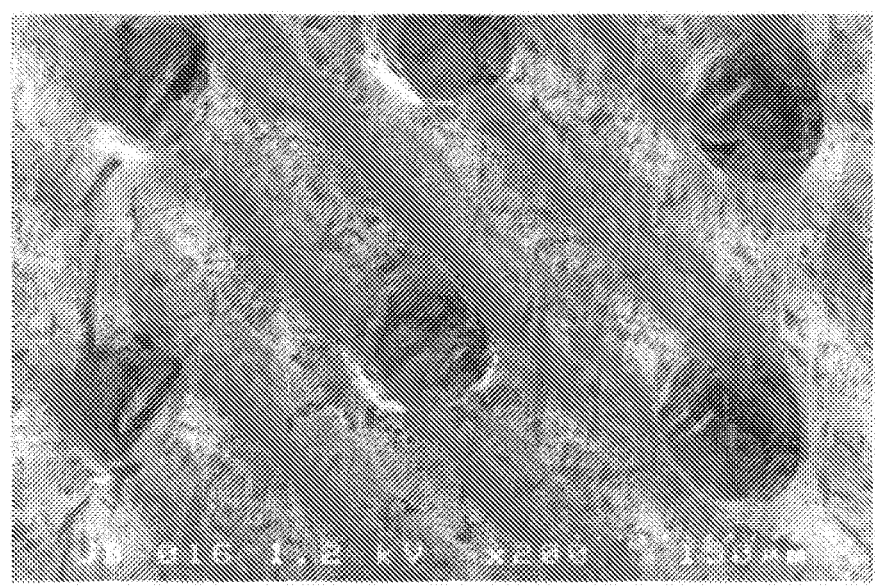

FIG. 2 is a scanning electron photomicrograph at 200× linear magnification of a surface illustrating an article having a distribution of conventional dimples or recesses.

Figure 3:
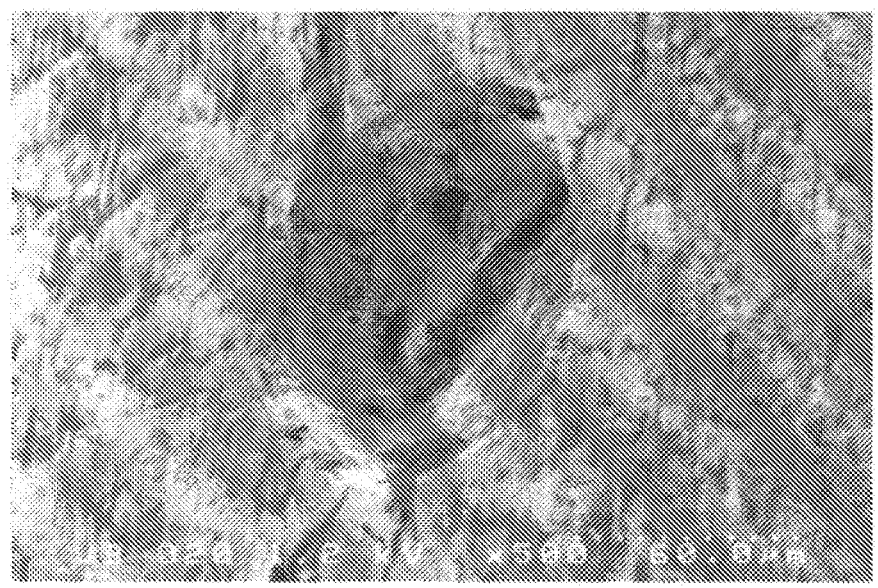

FIG. 3 is a scanning electron photomicrograph at 500× linear magnification of a surface illustrating a detail of a conventional dimple or recess.

Figure 4:
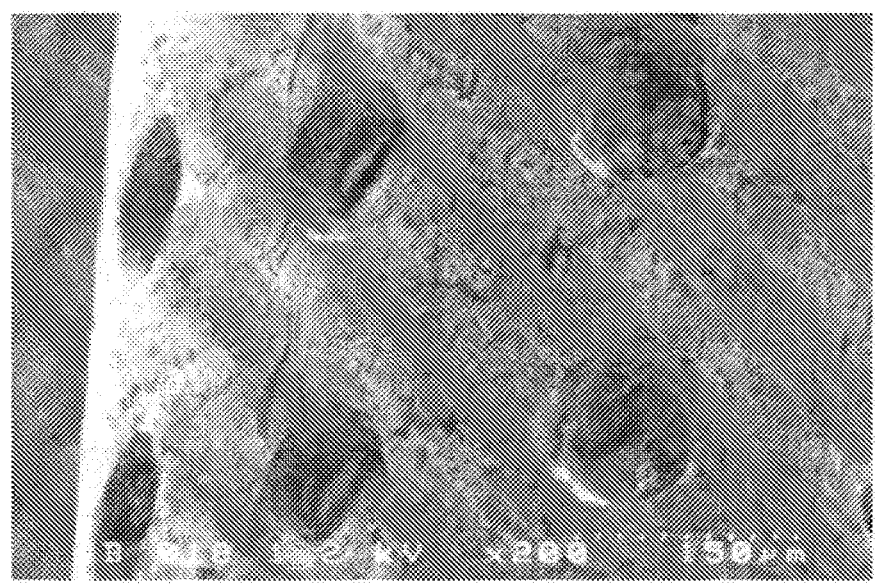

FIG. 4 is a scanning electron photomicrograph at 200× linear magnification of a surface illustrating an article having a distribution of conventional dimples or recesses.

Figure 5:
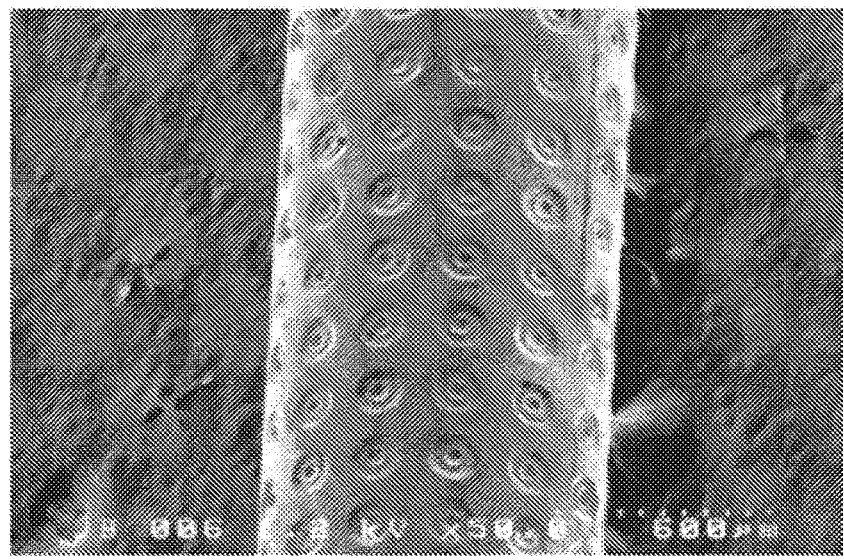

FIG. 5 is a scanning electron photomicrograph at 50× linear magnification of a surface illustrating an article having a distribution of exemplary compound or nested dimples; that is, a first partially spherical indentation and at least a second partially spherical indentation contained within the first indentation. The article is the shaft of a cannula or needle.

Figure 6:
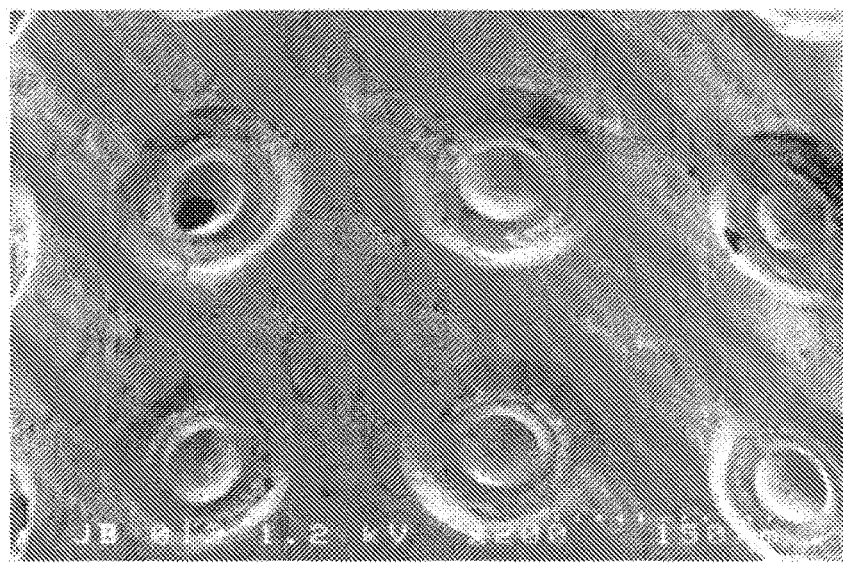

FIG. 6 is a scanning electron photomicrograph at 200× linear magnification of a surface illustrating an article having a distribution of exemplary compound or nested dimples; that is, a first partially spherical indentation and at least a second partially spherical indentation contained within the first indentation.

Figure 7:
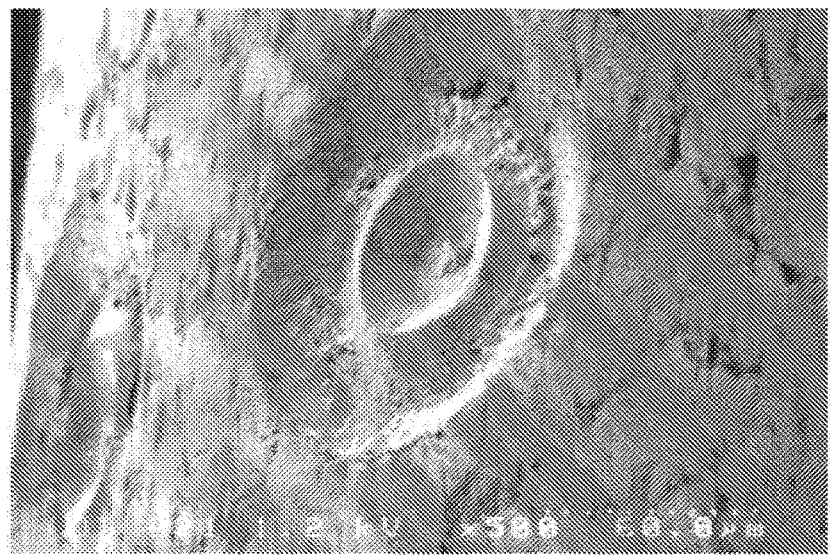

FIG. 7 is a scanning electron photomicrograph at 500× linear magnification of a surface illustrating a detail of an exemplary compound or nested dimple; that is, a first partially spherical indentation and at least a second partially spherical indentation contained within the first indentation.

Figure 8:
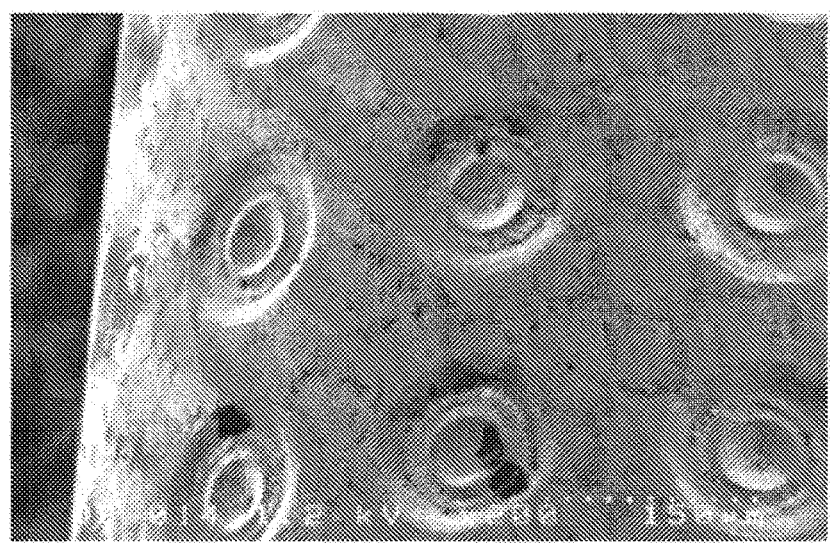

FIG. 8 is a scanning electron photomicrograph at 200× linear magnification of a surface illustrating an article having a distribution of exemplary compound or nested dimples; that is, a first partially spherical indentation and at least a second partially spherical indentation contained within the first indentation.

DETAILED DESCRIPTION OF THE INVENTION

The present invention provides an article or an interface having a surface that includes distribution of a first partially spherical indentation and at least a second partially spherical indentation contained within the first indentation. An exemplary configuration is illustrated in FIGS. 5-8 and such a multi-component or "compound" shape may be referred to as a "compound" or "nested" dimples or indentations. These "compound dimples" or indentions are etched or otherwise formed into a surface or interface of an article to enhance the ultrasonic imaging. Exemplary articles may be needles of the type used to conduct nerve blocks or the interface may be the surface of such a needle, cannula, catheter, catheter tip or similar article.

Referring more particularly to FIG. 7, the dimple or indention is composed of at least a first partially spherical indentation which is illustrated in the photomicrograph as the larger or major partially spherical indentation having a first radius of curvature. Fully contained within this first, larger or major partially spherical indentation is a second partially spherical indentation having a second radius of curvature. As can be seen in the FIGS. 5-8 and particularly in FIG. 7, the first partially spherical indentation has a larger radius of curvature than the second partially spherical indentation. In other words, the first partially spherical indentation has a lower curvature or is relatively flatter than the second partially spherical indentation—and the second partially spherical indentation has a higher curvature or is relatively steeper than the first partially spherical indentation.

According to an aspect of the invention, the first partially spherical indentation and the second partially spherical indentation are concentric. That is, the two indentations have a common center point and may be described as concentric circles when viewed from directly overhead as shown in FIG. 6.

In an aspect of the invention, the compound or nested dimples may be configured so the first partially spherical indentation contain or include a second and third (or more) partially spherical indentation—and these second or third or more partially spherical indentations will have a higher curvature will be relatively steeper than the first partially spherical indentation. Alternatively and/or additionally, the compound or nested dimples that may include at least a first partially spherical indentation and a second partially spherical indentation contained within the first indentation and a third (or more) partially spherical indentation contained within the second indentation.

In an aspect of the invention, the first (or major) partially spherical indentation or "dimple" may have a diameter ranging from about 0.003 to about 0.006 inch (about 76 micrometers to about 152 micrometers). The second (or minor) partially spherical indentation or "internal dimple" may have a diameter of up to about 0.0025 inch (about 63 micrometers). For example, the second (or minor) partially spherical indentation or "internal dimple" may have a diameter of from about 0.0005 to about 0.0025 inch (about 12 micrometers to about 63 micrometers). Additional partially spherical indentations contained within the first partially spherical indentation and/or the second partially spherical indentation should be smaller. It is contemplated that the first (or major) partially spherical indentations or "dimples" may have diameters ranging from about 0.003 to about 0.006 inch (about 76 micrometers to about 152 micrometers) and the second (or minor) partially spherical indentations or "internal dimples" may have diameters of up to about 0.0025 inch (about 63 micrometers). That is, the diameters of the first and/or the second partially spherical indentations may be non-uniform or polydisperse.

In an aspect of the invention, the spacing between the edges of separate adjacent major partially spherical indentations or dimples may be about 0.002 inch to about 0.01 inch apart (about 51 micrometers to about 254 micrometers apart). This distance is the closest distance between separate compound dimples as illustrated in FIGS. 5 and 6. For example, the distance between the edge of one dimple and the edge of the next closest dimple may be about 0.004 inch apart (about 102 micrometers apart). In yet another aspect of the invention, the depth of the partially spherical indentations may be from about 0.0005 to about 0.005 inch (from about 12 micrometers to about 126 micrometers). That is, the depth of the partially spherical indentations is the depth at the deepest portion of the compound or nested structure.

The "compound" structure of nested partially spherical indentations or dimples may be manufactured in a process using a laser. The second (or minor) partially spherical indentations or dimples are generated during the manufacturing process by spatter, displacement of metal and other phenomena. This "compound" or nested structure is thought to increase Rayleigh Scattering of an ultrasonic beam which significantly increases the echogenicity of an article (e.g., a needle) having a distribution of these "compound dimples". When the indentations are substantially smaller than the wavelength of the ultrasonic beam, Rayleigh Scattering occurs. It is thought that the "compound" structure of nested partially spherical indentations help generate Rayleigh Scattering and enhance ultrasonic imaging regardless of the incident ultrasonic beam angle.

As an example, a distribution of a first partially spherical indentation and at least a second partially spherical indentation contained within the first indentation (i.e., compound or nested partially spherical indentations or dimples) may be etched or manufactured along the length or only a portion of a metal needle of the type used to carry out peripheral nerve blocks. Such an exemplary configuration is illustrated in the scanning electron photomicrograph of FIG. 5. The distribution of the compound or nested "dimples" may be formed onto a cannula or needle blank. The cannula or needle blank can be further configured with a needle tip—also called a cutting tip. In the manufacturing process, forming the dimples first and added the cutting tip in a subsequent step allows the dimples to be present at or near the cutting tip of the needle. This is particularly advantageous because the compound or nested dimples provide enhanced ultrasonic imaging at or very near the tip of the needle or cannula. The present invention is readily distinguishable over more conventional recesses or dimples having generally flat bottoms and sides that are generally perpendicular to the needle surface and to the recess or dimple bottom as illustrated in FIGS. 1-4. In these photomicrographs, the recess or dimple bottom has a small groove which is believed to be an artifact of machining. As can be seen in the photomicrographs of FIGS. 1-4 and particularly in FIG. 3, the dimples are relatively deep compared to their diameters. Although it is believed to provide good reflectivity and scattering, this configuration is relatively difficult to manufacture. For example, the dimple depicted in FIG. 3 has a diameter of approximately 80 micrometers and a depth of approximately 40 micrometers.

As seen in the photomicrographs of FIGS. 5-8 and particularly in FIG. 7, the dimples of the present invention are much shallower than the conventional dimples shown in FIGS. 1-4. Shallower dimples are significantly easier to manufacture but are generally thought to have less reflectivity. However, the "compound" or nested structure is thought to increase Rayleigh Scattering of an ultrasonic beam. It is believed that the "compound" or nested structure significantly increases the echogenicity of the shallow dimple such that a shallow, relatively easy to manufacture dimple provides comparable reflectivity of ultrasonic beams as a relatively deep dimple. Accordingly, a surface (e.g., a needle) having a distribution of these easy to manufacture "compound dimples" has reflectivity that compares favorably to the difficult to manufacture deep dimples.

In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. An echogenic needle, comprising:
   a needle having a surface,
   wherein the surface includes a distribution of a plurality of first partially spherical indentations and a plurality of second partially spherical indentations, each of the plurality of first partially spherical indentations defining a first inner surface having a first radius of curvature, each of the plurality of second partially spherical indentations defining a second inner surface having a second radius of curvature, each of the plurality of second partially spherical indentations contained within a respective one of the first partially spherical indentations, the first radius of curvature being larger than the second radius of curvature such that each of the plurality of first partially spherical indentations is flatter than the each of the plurality of second partially spherical indentations,
   wherein the distribution of the plurality of first partially spherical indentations and the plurality of second partially spherical indentations is configured to enhance ultrasonic imaging.

2. The needle of claim 1, wherein each of the plurality of first partially spherical indentations is concentric with the respective one of the second partially spherical indentations.

3. The needle of claim 1, further comprising a plurality of third partially spherical indentations, wherein each of the plurality of third partially spherical indentations are contained within a respective one of the second partially spherical indentations.

4. The needle of claim 1, wherein each of the plurality of first partially spherical indentations comprises a first diameter and each of the plurality of second partially spherical indentations comprises a second diameter, the first diameter of the first partially spherical indentation ranging from 70 micrometers to 160 micrometers, the second diameter of the second partially spherical indentation ranging from 10 micrometers to 70 micrometers.

5. An echogenic catheter, comprising:
   a catheter having a surface,
   wherein the surface includes a distribution of a plurality of first partially spherical indentations and a plurality of second partially spherical indentations, each of the plurality of first partially spherical indentations defining a first inner surface having a first radius of curvature, each of the plurality of second partially spherical indentations defining a second inner surface having a second radius of curvature, each of the plurality of second partially spherical indentations contained within a respective one of the first partially spherical indentations, the first radius of curvature being larger than the second radius of curvature such that each of the plurality of first partially spherical indentations is flatter than the each of the plurality of second partially spherical indentations,
   wherein the distribution of the plurality of first partially spherical indentations and the plurality of second partially spherical indentations is configured to enhance ultrasonic imaging.

6. The catheter of claim 5, wherein each of the plurality of first partially spherical indentations is concentric with the respective one of the second partially spherical indentations.

7. The catheter of claim 5, wherein each of the plurality of first partially spherical indentations comprises a first diameter and each of the plurality of second partially spherical indentations comprises a second diameter, the first diameter of the first partially spherical indentation ranging from 75 micrometers to 160 micrometers, the second diameter of the second partially spherical indentation ranging from 10 micrometers to 70 micrometers.

8. The catheter of claim 7, wherein ore or more of the first and/or second diameters of the pluralities of first and/or the second partially spherical indentations are non-uniform.

9. The catheter of claim 5, further comprising a plurality of third partially spherical indentations, wherein each of the plurality of third partially spherical indentations is contained within a respective one of the plurality of second partially spherical indentations.

* * * * *